United States Patent [19]

Greene

[11] 4,207,904
[45] Jun. 17, 1980

[54] CONSTANT POWER DENSITY ELECTRODE ADAPTED TO BE USEFUL IN BIO-MEDICAL APPLICATIONS

[76] Inventor: Ronald W. Greene, 3116 S. 133rd St., Seattle, Wash. 98168

[21] Appl. No.: 945,514

[22] Filed: Sep. 25, 1978

Related U.S. Application Data

[63] Continuation of Ser. No. 763,544, Jan. 28, 1977, abandoned.

[51] Int. Cl.² ............................................. A61N 1/04
[52] U.S. Cl. .................................................... 128/798
[58] Field of Search ............... 128/798, 783, 791, 802, 128/803, 639–641, 644

[56] References Cited

U.S. PATENT DOCUMENTS

| | | | |
|---|---|---|---|
| 568,095 | 9/1896 | Muir | 128/798 |
| 1,989,282 | 1/1935 | Kimble et al. | 128/798 |
| 2,078,391 | 4/1937 | Last | 128/791 |
| 3,055,372 | 9/1962 | Browner | 128/798 |
| 3,464,416 | 9/1969 | Williams | 128/791 |
| 3,581,736 | 6/1971 | Zenkich | 128/641 |
| 3,606,881 | 9/1971 | Woodson | 128/641 |
| 3,750,094 | 7/1973 | Zenkich | 128/641 |
| 3,817,252 | 6/1974 | Maurer | 128/798 |
| 3,964,470 | 6/1976 | Trombley | 128/642 |
| 3,972,329 | 8/1976 | Kaufman | 128/641 |

FOREIGN PATENT DOCUMENTS

| | | | |
|---|---|---|---|
| 2414584 | 10/1975 | Fed. Rep. of Germany | 128/798 |
| 787477 | 7/1935 | France | 128/798 |
| 2288531 | 5/1976 | France | 128/791 |
| 6714179 | 4/1969 | Netherlands | 128/802 |

*Primary Examiner*—Lee S. Cohen
*Attorney, Agent, or Firm*—Cole, Jensen & Puntigam

[57] ABSTRACT

An electrode which is adapted to be used on a human body and suited for transmitting electrical impulses into the body. The electrode is relatively thin in cross-section and comprises in succession a lower layer of electrically conducting rubber, an intermediate layer of electrically conducting mesh or screen, and an upper layer of non-conducting rubber. An electrically conducting snap fastener is embedded in the electrode and is in electrical contact with the screen. The metal fastener provides a terminal connection for a conventional electrical lead, which carries the electrical impulses from a source thereof to the electrode.

3 Claims, 3 Drawing Figures

CONSTANT POWER DENSITY ELECTRODE ADAPTED TO BE USEFUL IN BIO-MEDICAL APPLICATIONS

This is a continuation, of application Ser. No. 763,544, filed Jan. 28, 1977, now abandoned.

BACKGROUND OF THE INVENTION

The present invention relates generally to the art of bio-medical electronics, and more specifically concerns an electrode which is used to transmit electrical energy to the human body.

Increasingly, electrical energy, usually in the form of pulses, is being used for diagnosing and treating various diseases and injuries. Additionally, electrical energy has been found to be useful in the rehabilitation of various portions of the body, particularly the limbs.

Typically, the electrical energy is applied to a specified area of the body by means of an electrode which is secured to the body by a direct adhesive, an adhesive strip, or similar means. The electrode receives the electrical energy, which is usually alternating or pulsed current, but may be direct current, through conventional electrical leads which are usually molded permanently into the electrode. The electrode in turn conducts the electrical energy into the specified area of the body.

Prior art electrodes have been found to have several substantial disadvantages. Generally, they are likely to produce slight burns equivalent ot an irritation on a user's skin, due to electrical hot spots in the electrode. The use of electrical energy thus has been somewhat restricted due to the potential for skin irritation. Furthermore, prior art electrodes are rather delicate and susceptible to tearing, and for that reason are often used only once and then discarded.

Additionally, in actual use, the molded electrode is frequently dislodged or displaced by abrupt movement of the body. There is often considerable difficulty in initially conforming prior art electrodes to the shape of the body on which they are placed, particularly in irregular areas. The prior art has relied upon the flexibility of rubber electrodes and an adhesive to maintain the electrodes in place on the body. The natural resilience of the rubber electrode, however, frequently results in a displacement of the electrode as it attempts to regain its original shape. All of these disadvantages have detracted from the general use of electrical energy on the human body.

Accordingly, a general object of the present invention is to overcome the disadvantages of the prior art noted above.

Another object of the present invention is to provide an electrode suitable for use on a human body which prevents electrical skin irritation by eliminating electrode hot spots.

A further object of the present invention is to provide such an electrode which reduces the amount of power applied to the body without reducing the treatment effectiveness of the electrical energy.

An additional object of the present invention is to provide such an electrode which is capable of compound deformation to conform to a particular portion of the human body and, further, which retains its deformed shape over a substantial period of time.

Yet another object of the present invention is to provide such an electrode which is not pulled off a user's skin by normal movement of the body.

It is a still further object of the present invention to provide such an electrode which resists tearing under normal use.

It is an additional object of the present invention to provide such an electrode which has a uniform low power density.

SUMMARY OF THE INVENTION

Accordingly, the present invention is an electrode which is particularly suited for use in those applications involving the transmission of electrical energy into a human body. The electrode includes an electrode terminal, an electrically conducting layer element in electrical contact with the terminal, and an electrically conducting interface in electrical contact with the conducting layer element. The electrode terminal is adapted to be connected through a conducting lead, conventional or otherwise, to a source of electrical energy. Usually, the electrical energy will take the form of a series of electrical pulses. The conducting layer element has a relatively large surface area compared to its thickness, and is so configured and arranged and comprises a material having such a conductivity that the resistance of the electrical path from the electrode terminal to any point on the conducting layer element is substantially equal, thus resulting in a uniform power density over its entire surface area. The conducting interface is made from a material which is suitable to be secured directly to the user's skin. In operation, electrical energy is supplied from the source through the conducting leads into the electrode terminal and then distributed over the entire surface area of the conducting layer element, from where it is transmitted directly to the user's skin through the conducting interface.

DESCRIPTION OF THE PREFERRED EMBODIMENT

Figure 1:
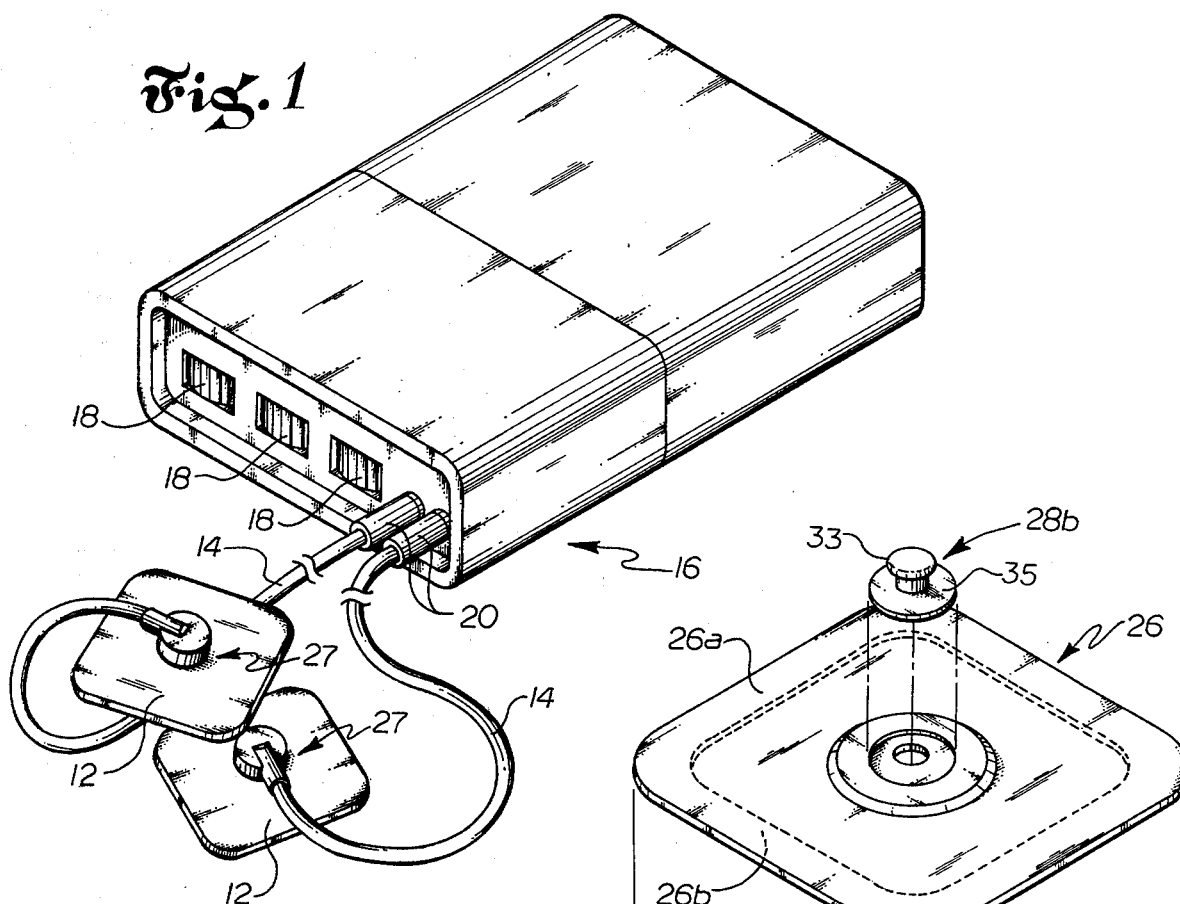
FIG. 1 is an isometric view showing the electrodes of the present invention in combination with a pair of conventional electrical leads and source of electrical energy.

The apparatus shown in FIG. 1 is a combination of electrodes 12—12 of the present invention, electrical leads 14—14, and a source of electrical impulses 16. When electrodes 12—12 are properly secured to the body of a user, the apparatus of FIG. 1 is ready for operation, and is useful for several bio-medical purposes, including diagnosis and treatment of injuries and diseases, and rehabilitation of injured or diseased limbs.

Characteristics of the electrical energy supplied by source 16 will vary somewhat, depending on the particular application. The structure of source 16, however, forms no part of the present invention, as a variety of electrical sources may be conveniently used.

In a corresponding application, Ser. No. 763,542, now U.S. Pat. No. 4,147,171, entitled PAIN CONTROL AND/OR MUSCLE STIMULATING AP- PARATUS by John L. Marshall and Ronald L. Greene, the named inventor in the present application, apparatus is disclosed and claimed which produces electrical impulses which have the effect of either reducing pain or stimulating muscle action. The subject matter of that application is incorporated by reference herein for purposes of background information.

Typically, source 16 will include a number of controls 18—18 which, if source 16 produces electrical pulses will control the various parameters of the pulses, such as pulse rate, pulse duration, and pulse voltage level. The output signal produced by source 16 is applied to electrical leads 14—14 through fairlead connectors 20—20, which comprise pin and socket connections. Generally, fairlead connectors 20—20 are of sufficient length to resist break-off of the pins on electrical leads 14—14 in normal operation.

At the other end of electrical leads 14—14 are electrodes 12—12 of the present invention. Instead of electrical leads 14—14 being molded into or otherwise permanently connected to electrodes 12—12, a connector 27 (to be described in more detail hereinafter), joins electrodes 12—12 to their respective electrical leads 14—14. Connector 27 permits electrical leads 14—14 to be conveniently connected/disconnected from electrodes 12—12. Connector 27 is adapted to permit rotation of electrode 12 about its electrical lead 14, as will be seen in further detail hereinafter.

Figure 2:
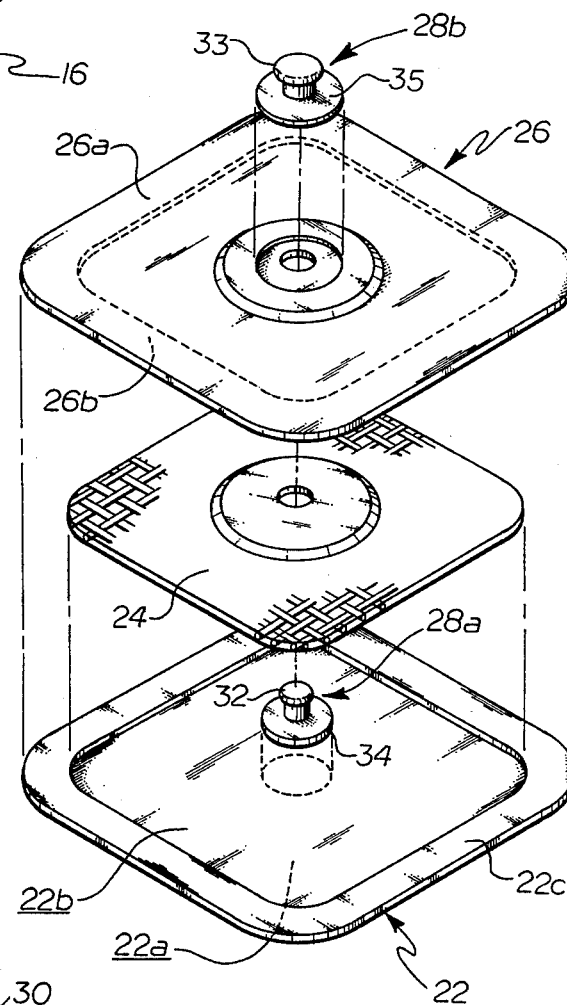
FIG. 2 is an exploded isometric view of the electrode of the present invention.
Figure 3:
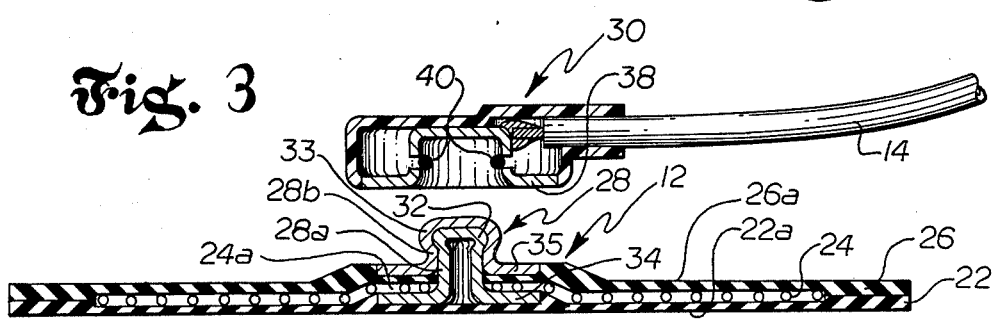
FIG. 3 is a cross-sectional view of the electrode of the present invention taken through the electrode terminal and of a conventional electrical lead adapted for connection to the electrode terminal.

Electrodes 12—12 may be conveniently secured, by an adhesive strip, patch or similar means, to the body of a user. FIGS. 2 and 3 show an exploded isometric view and a cross-sectional view, respectively, of the electrode of the present invention. FIG. 3 additionally shows a cross-section of that portion of the electrical lead which connects with a terminal on electrode 12, which together form connector 27.

Electrode 12 is, in the embodiment shown and described, relatively flat, and is thin compared to its other dimensions. The electrode shown is in the general form of square with rounded corners. The electrode may take other shapes, however, within the spirit of the invention. The size of the electrode is also not critical and will depend to a significant extent upon the particular application in which the electrode is used.

Electrode 12 comprises, in succession, a lower layer 22 of conducting rubber, an intermediate layer element 24 of electrically conducting mesh or screen having somewhat smaller outside dimensions than lower layer 22, an upper layer 26 of non-conducting rubber having the same outside dimensions as lower layer 22, and an electrode terminal in the form of a male snap fastener 28, which is in electrical contact with intermediate layer element 24 and which forms a portion of connector 27. Male fastener 28 protrudes above top surface 26a of upper layer 26 so as to be conveniently connectable to a female snap fasterer 30 attached to the end of electrical lead 14.

When molded together, the three layers 22, 24, 26 and male fastener 28 present a relatively thin, deformable, flexible electrode which may be conveniently secured to the body of a user and safely used for transmission of electrical impulses into the body.

Lower layer 22 comprises a relatively thin, approximately 1/64th of an inch, section of electrically conducting rubber. The rubber comprising lower layer 22 is made electrically conducting by embedding carbon particles therein, and is referred to as carbonized rubber. The bottom surface 22a of lower layer 22 is flat and otherwise suitable as an interface surface between electrode 12 and human skin. The material comprising lower layer 22 is sufficiently flexible to make good contact with the user's skin over its entire surface area, and can be maintained in good contact by use of conventional adhesive strips or the like. A water-soluble conductive jel is typically used between the electrode 12 and the skin to assist in maintaining good electrical contact therebetween.

Top surface 22b of lower layer 22 is somewhat irregular in outline since a first terminal portion 28a of male fastener 28 and the wire screen comprising intermediate layer element 24 are both embedded therein. First terminal portion 28a is embedded approximately at the center of lower layer 22 and protrudes upwardly therefrom. First terminal portion 28a comprises an inverted cylinder having open and closed ends. A generally outwardly extending peripheral lip or bulge 32 is included at the closed end thereof and an outwardly extending flange 34 is included at the open end thereof, extending at a right angle from the cylinder.

First terminal portion 28a is electrically conductive and positioned securely within lower layer 22 so that it will not dislodge therefrom. Flange 34 is separated from bottom surface 22a of lower layer 22 by a thickness of electrically conducting rubber of somewhat less than 1/64th of an inch.

Intermediate layer element 24 comprises a relatively thin, approximately 1/64th of an inch thick, electrically conducting wire mesh or screen. At the center of intermediate layer element 24 is an opening sufficiently large to permit intermediate layer 24 to be fitted past lip 32 of first terminal portion 28a and down against top surface 22b of lower layer 22. A portion 24a of intermediate layer element 24 is in electrical contact with flange 34 of first terminal portion 28a. The remainder of intermediate layer element 24 is embedded in, and in electrical contact with, lower layer 22.

Intermediate layer element 24 does not extend to the peripheral edge of lower layer 22. Hence, lower layer 22 has a narrow peripheral lip 22c which extends around both its own periphery and around the periphery of intermediate layer element 24. Peripheral lip 22c extends upward approximately half the thickness of intermediate layer element 24.

Upper layer 24 comprises a non-conducting, insulating rubber material and overlays intermediate layer element 24 and peripheral lip 22c of lower layer 22. Upper layer 26 extends laterally from the wall of first terminal portion 28a to the peripheral edge of lower layer 22. Upper layer 26 thus has a downwardly extending peripheral lip 26b which mates with the upwardly extending peripheral lip 22c of lower layer 22.

Embedded in upper layer 26, in mating electrical contact with first terminal portion 28a of male snap fastener 28, is a second terminal portion 28b thereof. Second terminal portion 28b is also an inverted cylinder having open and closed ends. At the closed end is a peripheral lip or bulge 33 extending outwardly therefrom. The upper part of second terminal portion 28b fits over and mates with the upper part of the first terminal portion 28a.

Second terminal portion 28b also includes a flange 35 which extends radially outwardly from the open end of second terminal portion 28b at substantially right angles thereto. The periphery of flange 35 is approximately coterminal with the periphery of first terminal portion 28a.

Second terminal portion 28b extends above top surface 26a of upper layer 26 a sufficient distance to permit connection with female snap fastener 30 attached to electrical lead 14. Typically, due to the thickness of flanges 34 and 35, the central portion of electrode 12 will be somewhat raised from the remainder thereof, as shown in FIGS. 2 and 3.

As mentioned above, electrode 12 although shown in the form of a relatively thin square, may also conveniently take other sizes and shapes. In many applications, a rectangular shape is preferred, with dimensions of 2 inches by 6 inches, or 2 inches by 8 inches, being relatively common sizes. Generally, 2 inches by 2 inches is the recommended minimum size, so that the power density of the electrical energy over the surface area of electrode is kept low.

As stated above, lower layer 22 is comprised of a conducting rubber, the bottom surface 22a of which acts as an interface between the electrode and the user's body. Although a carbon impregnated rubber is used in the embodiment shown and described, other materials which are capable of providing a conducting interface between intermediate layer element 24 and the user's body may be used. Carbonized rubber has been found to be further useful in that it is capable of compound (two-plane) deformation, and further that it is capable of withstanding sterilization processes, so that the electrodes may be repeatedly used.

A wire mesh or screen is desirable for use as the intermediate layer element 24 because it provides a number of operating advantages. Although various mesh sizes can be conveniently used, a #50 mesh has been found to work satisfactorily. The wire mesh comprising layer element 24 is electrically conductive and has a conductivity such that the resistance of the electrical path from male snap fastener 28 to any point on layer element 24 is substantially the same. These features result in an intermediate layer, and hence an electrode, which has uniform power density over virtually its entire surface area, a significant advantage over prior art bio-medical electrodes.

Such a structure eliminates the hotspots found in prior art electrodes in the vicinity of their physical contact with the electrical leads, and thus eliminates the resulting electrical skin irritation. By providing an electrode with uniform power density, electrical devices may be used in a substantial greater number of applications than has heretofore been advised.

This particular advantage may be secured by various mesh configurations, and even a solid thin sheet, as long as the resistance of the current path from the point of contact with the source of electrical energy to any particular point on intermediate layer element 24 is substantially the same.

Certain additional significant advantages accrue, however, when a wire screen is used for intermediate layer element 24. With a screen, electrode 12 may be easily and conveniently shaped or deformed to conform to the outline of virtually any portion of the user's body. Furthermore, electrode 12 will remain in that shape because of the compound deformation permitted by a screen structure. Electrode 12 thus is capable of taking compound shapes, to accommodate various body contours. Furthermore, electrode 12 is able to maintain its deformed shape, instead of rebounding gradually into its original shape as is the case with prior art bio-medical electrodes.

Another advantage to the use of a screen is that it is easily embedded into lower layer 22. A solid sheet would require special surface preparation to insure an adequate bond between it and the lower layer 22. Hence, the wire mesh configuration provides advantages in addition to uniform power density.

Upper layer 26, although described as being of insulating rubber, may be comprised of any of a large number of materials, as long as the selected material is flexible and insulating, so that it provides protection for the user or other persons who accidentally or otherwise come into contact with the top of the apparatus during operation.

Electrical lead 14 connects the source of electrical energy 16 to electrode 12. At the end of each lead mating with electrode 12 is a female snap fastener 30 which in the embodiment shown is adapted to receive male snap fastener 28, which is embedded in electrode 12. Female snap fastener 30 is generally an inverted U-shaped cylinder with a flange 38 which extends outwardly from its open end substantially at right angles thereto. Flange 38 mates with flange 35 of upper terminal portion 28b in intimate electrical contact.

Near the open end of female snap fastener 30 are a pair of spring clips 40—40, which are pushed back when female snap fastener 30 is pushed downward over male snap fastener 28. As the upper lip 33 of terminal portion 28b passes over spring clips 40—40 they spring back to their original position, thus holding the male and female snap fasteners in intimate electrical contact.

The snap fastener arrangement described above, although known in the art per se, has a significant advantage when used in the structure shown and described. Not only does it permit selective connection and disconnection of an electrical lead from its associated electrode, but further, it is not rotatably fixed, so that electrical lead 14 is free to rotate about electrode 12. This is a significant advantage in that normal movement of the body will not result in undue strain on the electrical leads or a pull-off of the electrode from the user's body.

Hence, although the connection 27 between electrical lead 14 and electrode 12 shown and described is not necessarily critical to the invention, it does have important advantages in certain applications. Other conventional connection devices affording the same advantages may, of course, by used in place of the one shown.

Thus, a new electrode has been described which is particularly suitable for use on human beings. The invention is significant in that it eliminates electrical skin irritation by means of a uniform low power density. This is made possible by a structure which includes an intermediate layer element comprising a material having a conductivity such that there is substantially equal electrical resistance from the electrode terminal which receives the electrical energy to any point on the layer element. A lower conductive-rubber layer is provided which acts as a conducting interface between the electrode and the skin, and an upper insulating layer protects the user and others from extraneous electrical contact.

Although an exemplary embodiment of the invention has been disclosed herein for purposes of illustration, it should be understood that various changes, modifications and substitutions may be incorporated in such embodiment without departing from the spirit of the invention which is defined by the claims which follow.

What is claimed is:

1. A reusable electrode which is particularly suitable for use in bio-medical applications on human beings, comprising:
   a. a flexible, electrically conducting, relatively thin lower element, approximately 1/64th inch thick, having upper and bottom surfaces and a narrow peripheral lip on the upper surface thereof defining a recess area, wherein the bottom surface of said lower element is suitable for contact with the skin of human users and conformable to the contours of the human body;
   b. an electrically conducting, relatively thin, approximately 50-mesh metal screen intermediate element, approximately 1/64th inch thick, embedded in the lower element in said recess area thereof so that said intermediate element is in intimate electrical contact with said lower element and is bounded by said peripheral lip, said metal screen being capable of compound deformation without distortion;
   c. a flexible, electrically insulating, relatively thin, upper element overlaying said intermediate element and said peripheral lip of the lower element; and
   d. terminal means located approximately central of said electrode and in direct electrical contact with said intermediate element, said terminal means being connectable, through a conducting lead, or the like, to a source of electrical energy; wherein the combination of the mesh size and thickness of said metal screen and the thickness of said lower element is such that a substantially equal low resistance path exists between said terminal means and any other point on the bottom surface of said lower element, so that there is a substantially uniform power density over the bottom surface of said lower element, and wherein said metal screen is sufficiently rigid, due to its thickness and mesh size, that when the electrode is deformed from a rest configuration to a desired configuration, said electrode is prevented from recovering toward the rest configuration, so that the electrode remains in said desired configuration without restraint.

2. An article of claim 1, wherein the material comprising said lower element is electrically conductive rubber.

3. An article of claim 1, wherein said terminal means includes a base flange portion which is in electrical contact with said intermediate element, an upstanding portion which projects upwardly from said flange portion and a cap portion which mates with said upstanding portion, said cap portion having a lower flange, the edge of which abuts said upper element, said cap portion being configured to receive an electrical connector on the conducting lead from the source of electrical energy.

* * * * *